US005554536A

United States Patent [19]

Rising

[11] Patent Number: 5,554,536
[45] Date of Patent: Sep. 10, 1996

[54] BIOLOGICAL ANALYSIS DEVICE HAVING IMPROVED CONTAMINATION PREVENTION

[75] Inventor: Donald B. Rising, Stow, Mass.

[73] Assignee: Millipore Investment Holdings Limited, Wilmington, Del.

[21] Appl. No.: 369,212

[22] Filed: Jan. 5, 1995

[51] Int. Cl.⁶ .................................................. C12M 3/06
[52] U.S. Cl. .................... 435/305.1; 422/102; 436/809; 435/288.3; 435/288.5; 435/305.2; 435/809
[58] Field of Search ............................... 422/101, 102; 436/809; 435/809, 288.4, 305.2, 288.5, 288.3, 305.1

[56] References Cited

U.S. PATENT DOCUMENTS

| | | | |
|---|---|---|---|
| 3,986,534 | 10/1976 | Schmidt | 141/1 |
| 4,154,793 | 5/1979 | Guigan | 422/55 |
| 4,426,451 | 1/1984 | Columbus | 436/518 |
| 4,689,203 | 8/1987 | Kuusisto | 422/72 |
| 4,734,192 | 3/1988 | Champion et al. | 210/335 |
| 5,215,920 | 6/1993 | Lyman et al. | 435/284 |
| 5,279,791 | 1/1994 | Aldrich | 422/58 |
| 5,310,523 | 5/1994 | Smethers | 422/57 |

Primary Examiner—David A. Redding
Attorney, Agent, or Firm—Andrew T. Karnakis

[57] ABSTRACT

A device for conducting biological analysis, such as cell culture, is disclosed having improved contamination prevention features. In a preferred embodiment, a microwell membrane plate for cell analysis is adapted to be inserted into a shallow rectangular tray with elevated side walls which form a single large reservoir for holding an appropriate liquid used in cell growth and analysis. The side surfaces of the tray include a raised ridge extending about the entire periphery of the tray. A series of uniform-height steps formed on the ridge serve as support for the microwell membrane plate when inserted into the tray and also create a narrow capillary gap between the plate and the tray. A ledge extending laterally from the base of the ridge forms a second, wider gap when the microwell membrane plate is inserted into the tray. The height of the first capillary gap is less than the height of the second gap formed within the zone of space extending to the exterior of the device, thus when the tray and plate are tilted, as when jostled during handling, liquid from the reservoir will preferentially remain in the space formed by the first capillary gap. Liquid which does spill into the second gap will run back into the reservoir when the device is leveled.

9 Claims, 2 Drawing Sheets

BIOLOGICAL ANALYSIS DEVICE HAVING IMPROVED CONTAMINATION PREVENTION

BACKGROUND OF THE INVENTION

This invention relates generally to devices for carrying out biological analyses, particularly in vitro processes involving living cells such as cell culture and subsequent assays evaluating cell function. More particularly, this invention relates to multi-welled cell culture plates with permeable membranes sealed to the bottom of each of the wells.

The technology explosion associated with the biotech industry has seen a concomitant growth in the "biotechware" industry, where the need for a variety of dishes, flasks, tubes and plates to support biological studies is paramount. In many experiments involving biomolecules there is a stringent requirement to maintain sterile conditions as much as possible. This is particularly the case in carrying out in vitro processes involving living cells.

Devices used in conjunction with the in vitro growth and subsequent analysis of living cells are available from a number of manufacturers such as A/S Nunc and Corning. Such devices are available in various forms ranging from large plastic flasks, to which media and/or reagents are added to culture or assay the living cells, to plates having a plurality of self-contained impermeable plastic wells (usually available in 6-, 12- or 24-well versions), in which cell culture media or biological reagents are added to each individual well.

It has been shown that benefits ensue when cells are grown and studied with the aid of a permeable microporous membrane suspended in the cell growth medium. The microporous membrane usually is sealed to one end of a plastic cylinder which then is placed into a well of a culture plate with culture medium. Cells are placed in the chamber above and sometimes below the membrane. The microporous membrane allows free diffusion of ions and molecules so that cells more closely resemble their in vivo state than when grown on solid, impermeable plastic surfaces. The membrane allows liquid access to both sides of the cell, thereby improving cell differentiation and facilitating studies of cell transport and permeability as well as cell-cell interactions. The Millicell® culture plate insert sold by Millipore Corporation is an example of such a membrane device.

More recently, the concept of providing membrane wells for cell studies has been expanded to provide multiple-well plates having an array of wells with open bottoms and a microporous membrane sealed to the bottom of each well (hereinafter referred to as a "microwell membrane plate"). The microwell membrane plate is adapted to be inserted into a tray having a mating pattern of closed-end wells. Tissue culture media and/or reagents can be provided above and below the membranes, and cells can be added as desired to perform multiple studies simultaneously. The filter plate element of a MultiScreen® plate sold by Millipore Corporation is an example of such a microwell membrane plate.

Often it is desired to grow cells on the surface of the microporous membranes for several days before undertaking cell biology studies in order to allow attachment dependent cells to form a confluent layer on the membrane and to express their fully differentiated anatomical and physiological functions. A multi-welled tray of the type described above having mating closed-end wells can be used with a microwell membrane plate during the cell growth period; however, the culture media must be changed often to replenish nutrients used by the growing cells. It is advantageous during this initial growth period to use a tray with a few large reservoirs or even a single large reservoir which accepts all the filter wells of the microwell membrane plate. The large tray reservoirs provide a greater volume of culture medium per well than can a reservoir which accepts only one filter well, thus the medium does not have to be changed as often. Also, it is easier to change the culture medium in a single large reservoir rather than to change it in as many as 96 small reservoirs per tray.

Regardless of the type of device employed, experimentation involving living cells requires attention to sterility. Microbiological contamination is always an important concern when handling living cells. However, in this regard, it is not possible to hermetically seal the plates housing the growing cells from the ambient environment because an exchange of gas from the cells to the external environment and vice-versa is necessary. Thus covers which are used with such plates must provide a space between the cover and the container housing the cells. During handling of these cell analysis devices, the liquid solutions employed may spill and remain in the space between the cover and the container. This provides a pathway for contamination to enter the container.

The foregoing problem associated with spillage becomes magnified when dealing with a microwell membrane plate, such as the aforementioned MultiScreen® device, when used with a tray which has a single reservoir for media to interface with all cell-containing wells through the membrane. In this instance, the tray reservoir is relatively large and is filled almost to its rim with liquid. Since the tray cannot be sealed to the plate (or a cover for the plate), spillage is likely when the tray and plate are tilted or jostled during handling. Thus liquid will readily seep into the space between the tray and plate and remain there, thereby creating a contamination pathway which could adversely effect the cells or any subsequent analysis performed thereon.

SUMMARY OF THE INVENTION

The present invention overcomes the disadvantages and limitations of prior art devices by providing an improved biological analysis device which utilizes capillary forces to eliminate a contamination liquid pathway by which microbiological contaminants may enter the interior of the device from the ambient environment. In a preferred embodiment, a microwell membrane plate for cell analysis is adapted to be inserted into a shallow rectangular tray with elevated side walls which form a single large reservoir for holding an appropriate liquid used in cell growth and analysis. Each well of the plate fits within the reservoir to expose its corresponding membrane to the cell reagent liquid. The side surfaces of the tray include a raised ridge extending about the entire periphery of the tray. A series of uniform-height steps formed on the ridge serve as support for the microwell membrane plate when inserted into the tray and also create a narrow capillary gap between the plate and the tray.

In the foregoing embodiment of the invention, the raised ridge protrudes along the innermost edge of the tray (i.e. closest to the reservoir) and a ledge extending laterally from the base of the ridge forms a second, wider gap when the microwell membrane plate is inserted into the tray. This second gap extends uniformly to the outermost edge of the plate and tray combination and in conjunction with the first gap forms a pathway for the exchange of gases between the cells in the reservoir and the external environment. In accordance with an important aspect of the invention, the height of the first gap is less than the height of the second gap formed within the zone of space extending to the exterior of the device. In this manner, when the tray and plate are tilted, as when jostled during handling, liquid from the reservoir will preferentially remain in the space formed by the first capillary gap. Liquid which does spill into the second gap will run back into the reservoir when the device is leveled.

These and other aspects and advantages of the present invention will become apparent from the following detailed description with reference to the drawings.

DETAILED DESCRIPTION OF THE INVENTION

Figure 1:
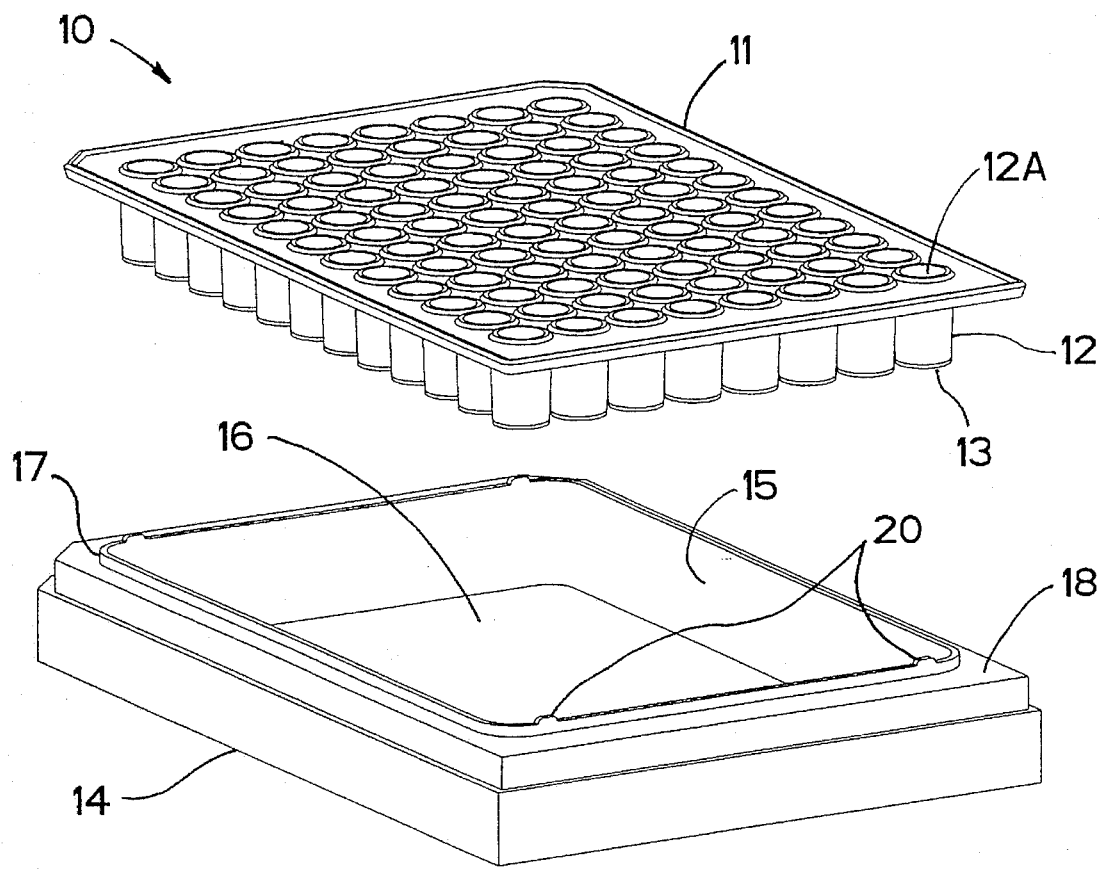
FIG. 1 is an exploded view in perspective of a microwell membrane plate and reservoir tray in accordance with a preferred embodiment of the invention.

FIG. 1 shows a preferred embodiment of a device 10 used for cell culture. Although this embodiment is described in the context of cell culture, the device may be used in any number of ways for studying in vitro living cells, such as used to perform assays for analyzing cell function.

The device 10 includes a microwell plate 11 having ninety-six (96) individual plastic wells 12 with open ends 12A and a permeable membrane 13 sealed to the bottom of each of the wells. The plate is formed from a suitable material such as polystyrene and the membrane is a microporous membrane made from cellulose esters, polyvinylidene fluoride (PVDF) or any other suitable material. The pore size of the membrane for the device 10 can range from 0.1 to 20 microns. Devices used for other applications requiring ultrafiltration membranes will have pore sizes less than 0.1 microns. A rectangular tray 14 made of a suitable material such as glycol modified polyethylene terephthalate (PETG) includes elevated side walls 15 defining a shallow reservoir 16 which occupies essentially the entire area of the tray. The dimensions of the reservoir are such that all of the 96 wells may be inserted within the reservoir when the plate and tray are combined during cell culture.

Figure 2:
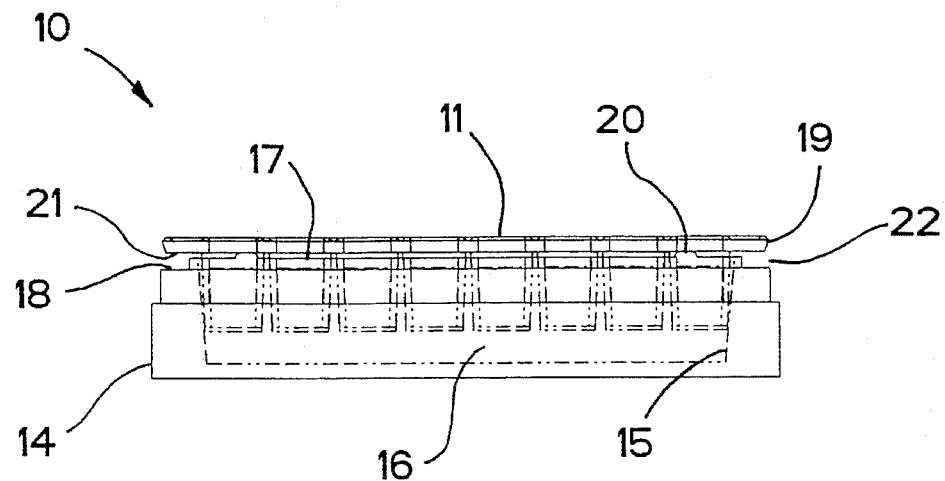
FIG. 2 is an end view of the plate of FIG. 1 inserted into the tray.
Figure 3:
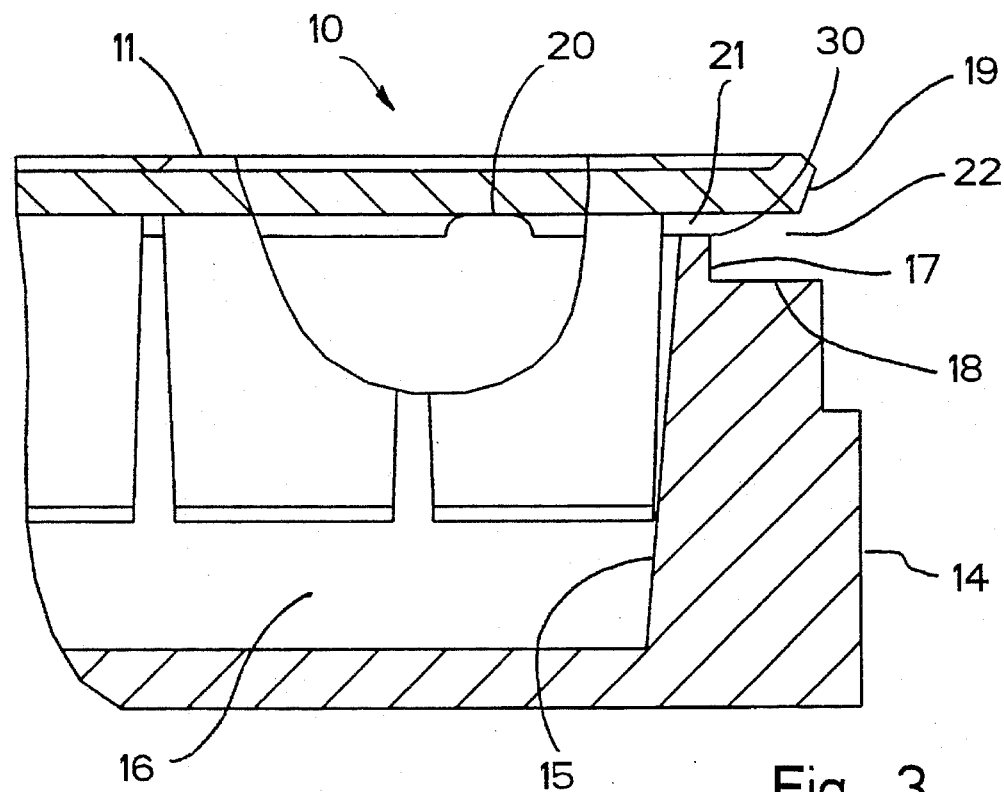
FIG. 3 is an enlarged end view in section of the assembled device of FIG. 2 partially cut away to show details of the gaps and spaces formed when the plate is inserted into the tray.

The tray 14 includes a raised ridge 17 located along the innermost edge of the tray adjacent to the reservoir 16 about the entire periphery of the tray. A ledge 18 is disposed substantially at right angles to the side walls 15 and extending laterally from the base of the raised ridge. As best shown in FIGS. 2 and 3, the outer edge 19 of the plate 11 extends to approximately the same width as that of the ledge when the plate is inserted into the tray.

Four steps 20 of uniform height formed on the raised ridge 17 at opposite ends of the tray 14 serve to support the plate 11 and also create a capillary gap 21 between the tray and plate near the reservoir 16. As shown, a second, much wider gap 22 is also formed in the vicinity of the outer edge 19 of the plate when the plate is inserted in the tray. The space between the tray and plate at this location defines the external interface between the ambient environment and the interior of the device 10. In accordance with an important aspect of the invention, the height of the capillary gap 21 is less than the height of the gap 22; additionally, there is no space in the zone between the capillary gap and the exterior of the device 10 whose height is as low as or lower than the gap 21. A cover (not shown) is placed over the device during cell culture and the combination of the cover, the plate, the tray and both gaps 21 and 22 form a narrow, tortuous path which minimizes the chances for contamination during cell culture while still allowing the necessary exchange of gases.

As mentioned, sterility is an important consideration for cell culture applications; however, it is not desirable to hermetically seal the device 10 because this would obviate the ability to exchange $CO_2$ and $O_2$ gas between the cells and the ambient environment. Thus spillage of growth media during handling is a potential source of microbiological contamination. If the medium stagnates and remains in contact with the external environment, a pathway for microbiological contaminants to enter the device will result due to the presence of a continuous liquid path directly to the reservoir 16. To overcome these difficulties, the height of the capillary gap 21 is kept as small as possible consistent with the need to allow gas exchange. Heights of between 0.01 mm and 1.0 mm have been found to be particularly advantageous. On the other hand, the height of the second gap 22 is made significantly larger than that of the gap 21, for example, between 0.1 mm and 5.0 mm. Heights of the gap 22 can be several times the height of the gap 21. That is to say, if the capillary gap is 0.2 mm the second gap will be 1.0 mm or thereabouts. Thus when the device 10 is tilted and liquid spills from the reservoir 16 it will preferentially remain in the capillary gap 21 where it is isolated from the contaminating external environment because of the absence of liquid in the second, larger gap 22.

Other considerations which influence the creation of the above described liquid barrier involve the selection of materials having appropriate surface wetting properties relative to the cell culture liquid. It would be preferred to have both the plate 11 and the tray 14 made of materials that were not wetted by the cell culture liquid. That is, when the contact angle of the liquid on both surfaces is greater than 90°, the liquid will not enter the gap 21 except under the influence of some pressure. However, materials having such wetting properties often are not acceptable for other reasons. The device 10 also will prevent contamination of the cell culture liquid if the plate 11 and the tray 14 are made of materials that the cell culture liquid wets but on which it will not spread. The cell culture liquid will not spread if it makes a contact angle of less than 90° but greater than 0° with the solid surfaces. Under these conditions, the cell culture liquid may spill beyond the capillary gap 21 into the second gap 22; however, any culture liquid which remains in the gap 22 will return to the reservoir 16 when the device is once again leveled. For certain applications the inclusion of a sharp edge 30 at the interface between the capillary gap 21 and the second gap 22 will enhance the liquid barrier performance.

Figure 4:
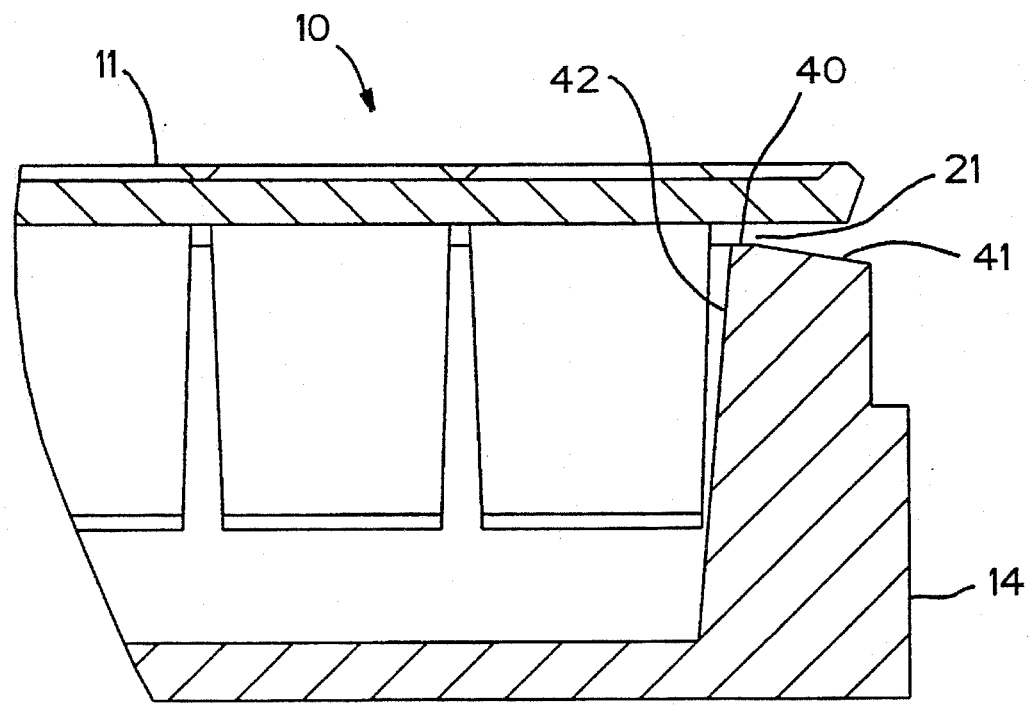
FIG. 4 is an enlarged end view in section of an alternate embodiment.

FIG. 4 shows an alternate embodiment for the device 10 wherein the ridge is of different construction. In this embodiment, a ridge 40 is formed between two slopes defined by tapered ledge 41 and perpendicular side wall 42. The ledge 41 tapers from a narrow height with respect to the plate 11 at the innermost edge of the tray 14 to a wider height at the outermost edge of the tray. In this instance, the wide end would not need to be much wider than the narrow end. It is also possible to taper the ledge in the opposite direction as long as the taper does not create a space whose height is less than the capillary gap 21.

The invention is not intended to be limited by the foregoing examples as still other modifications may be possible or will become apparent to those of skill in the art without departing from the scope of the present invention.

I claim:

1. A device for conducting biological analyses comprising:

a tray with a bottom surface and contiguous side surfaces defining at least one reservoir for holding a liquid solution;

a ledge extending around the periphery of said reservoir;

means defining a ridge on said ledge between the interior of said reservoir and the exterior of said tray;

sample receptacle support means adapted to cover the opening of said reservoir at least in the vicinity of said ridge and said ledge;

means for spacing said support means from said ridge to create a first capillary space therebetween extending about the periphery of said reservoir to permit the exchange of gas from the exterior of said device to the interior of said reservoir and vice-versa;

said ledge and said support means creating a second space adjacent to said first capillary space, the height of said first capillary space being less than that of said second space, whereby said liquid solution in said reservoir will preferentially remain in said first capillary space in the event said liquid solution spills out of said reservoir.

2. The device of claim 1 wherein said support means includes at least one containment means having a permeable membrane sealingly attached thereto such that said membrane is positioned to contact said liquid solution in said reservoir.

3. The device of claim 2 wherein said containment means includes living cells for cell culture.

4. The apparatus of claims 1, 2 or 3 wherein at least one of the surfaces which define said first capillary space and said second space has surface properties such that said liquid solution will have a contact angle of less than 90° but greater than 0° with said at least one surface.

5. The apparatus of claims 1, 2 or 3 wherein the height of said first capillary space is between 0.01 mm and 1 mm.

6. The apparatus of claims 1, 2 or 3 wherein the height of said second space is between 0.1 mm and 5 mm.

7. The apparatus of claims 1, 2 or 3 wherein the transition from said first capillary space to said second space is a sharp edge.

8. The apparatus of claims 1, 2 or 3 wherein the height of said second space increases with distance from said first capillary space.

9. The apparatus of claims 1, 2 or 3 wherein the height of said second space decreases with distance from said first capillary space.

* * * * *